United States Patent
Diehr

[11] Patent Number: 5,382,671
[45] Date of Patent: Jan. 17, 1995

[54] PROCESS FOR THE PREPARATION OF 2-CHLORO-5-ALKYLAMINOMETHYL-PYRIDINES

[75] Inventor: Hans-Joachim Diehr, Wuppertal, Germany

[73] Assignee: Bayer Aktiengesellschaft, Leverkusen, Germany

[21] Appl. No.: 15,507

[22] Filed: Feb. 9, 1993

[30] Foreign Application Priority Data

Feb. 19, 1992 [DE] Germany .............................. 4204919

[51] Int. Cl.[6] .................. C07D 213/26; C07D 213/40; C07D 213/36; C07D 213/56
[52] U.S. Cl. .................................... 546/329; 546/334; 546/336
[58] Field of Search .......................... 546/329, 334, 336

[56] References Cited

FOREIGN PATENT DOCUMENTS

| | | | |
|---|---|---|---|
| 0302389 | 2/1989 | European Pat. Off. | 546/334 |
| 0366085 | 5/1990 | European Pat. Off. | 544/333 |
| 0376279 | 7/1990 | European Pat. Off. | 546/334 |
| 0379928 | 8/1990 | European Pat. Off. | 546/265 |
| 0425030 | 5/1991 | European Pat. Off. | 546/334 |

*Primary Examiner*—Alan L. Rotman
*Attorney, Agent, or Firm*—Sprung Horn Kramer & Woods

[57] ABSTRACT

The invention relates to a new process for the preparation of 2-chloro-5-alkylaminomethyl-pyridines of the formula (I)

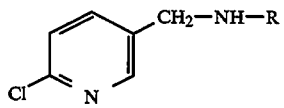

in which R represents alkyl.

In this process, 2-chloro-5-aminomethyl-pyridine is reacted with formic acid at temperatures between 20° C. and 200° C., if appropriate in the presence of a diluent, the 2-chloro-5-formylaminomethyl-pyridine which has been formed in this process is reacted without intermediate isolation (in situ) with alkylating agents at temperatures between 0° C. and 100° C., if appropriate in the presence of an acid acceptor, if appropriate in the presence of a diluent, and, finally, the 2-chloro-5-(N-alkyl-N-formyl-aminomethyl)-pyridines thus formed of the general formula (V)

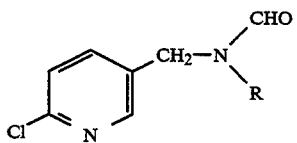

in which

R has the abovementioned meaning, are reacted with aqueous alkali metal hydroxide solution at temperatures between 20° C. and reflux temperature, if appropriate after volatile components have been distilled off.

The compounds (I) are, for example, intermediates for the preparation of insecticidally active substances.

10 Claims, No Drawings

PROCESS FOR THE PREPARATION OF 2-CHLORO-5-ALKYLAMINOMETHYL-PYRIDINES

The invention relates to a new process for the preparation of 2-chloro-5-alkylaminomethyl-pyridines.

It is known that 2-chloro-5-alkylaminomethyl-pyridines are obtained when 2-chloro-pyridine-5-carboxaldehyde is first reacted with alkylamines and, in a second step, the resulting alkylimino compounds are treated with hydrogenating agents such as, for example, sodium boranate (cf. EP-A 302,389).

It is furthermore known that 2-chloro-5-methylaminomethyl-pyridine can be obtained by reacting 2-chloro-5-chloromethyl-pyridine with methylamine (cf. EP-A 366,085, EP-A 376,279, GB-A 2,228,003, EP-A 425,030).

However, the yields which can be achieved and the qualities of the products are not always satisfactory in both known synthesis methods.

It has now been found that 2-chloro-5-alkylaminomethyl-pyridines of the general formula (I)

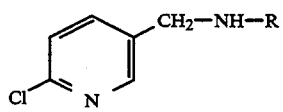  (I)

in which
R represents alkyl, are obtained in very good yields and in high purity when 2-chloro-5-aminomethyl-pyridine of the formula (II),

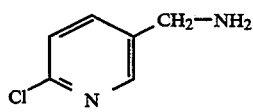  (II)

is reacted with formic acid at temperatures between 20° C. and 200° C., if appropriate in the presence of a diluent,
the 2-chloro-5-formylaminomethyl-pyridine which has been formed in this process, of the formula (III),

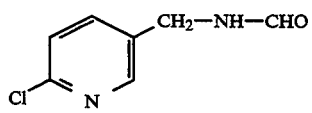  (III)

is reacted without intermediate isolation (in situ) with alkylating agents of the general formula (IV)

R—X  (IV)

in which
X represents halogen or the group —O—SO$_2$—O—R and
R has the abovementioned meaning, at temperatures between 0° C. and 100° C., if appropriate in the presence of an acid acceptor, if appropriate in the presence of a catalyst and if appropriate in the presence of a diluent,
and, finally, the 2-chloro-5-(N-alkyl-N-formyl-aminomethyl)-pyridines thus formed of the general formula (V)

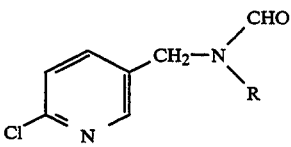  (V)

in which
R has the abovementioned meaning, are reacted with aqueous alkali metal hydroxide solution at temperatures from 20° C. to reflux temperature, if appropriate after volatile components have been distilled off.

Surprisingly, the process according to the invention allows 2-chloro-5-alkylaminomethyl-pyridines of the formula (I) to be obtained in very good yields and in high purity, even though three reaction steps are involved and no intermediate isolation and thus no purification of intermediates takes place.

The course of the reaction in the process according to the invention can be outlined for example by the following equation:

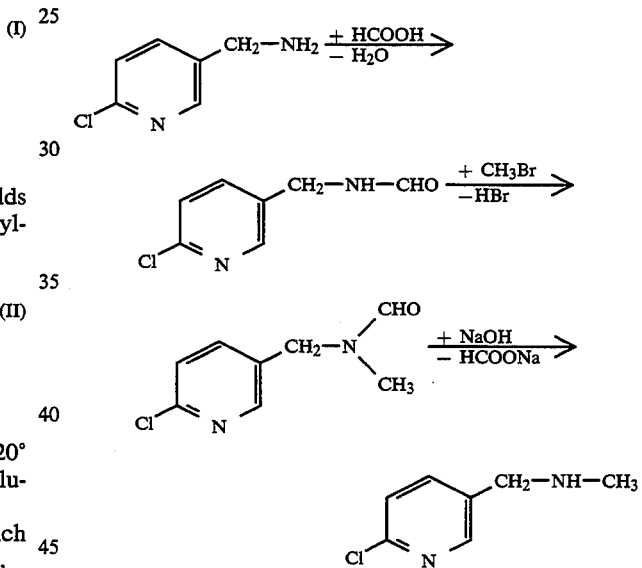

The process according to the invention preferably relates to the preparation of compounds of the formula (I) in which
R represents straight-chain or branched alkyl having 1 to 6 carbon atoms.

Compounds of the formula (I) which are prepared by the process according to the invention are, in particular, those in which
R represents methyl, ethyl, propyl, isopropyl, butyl, isobutyl or sec-butyl.

2-Chloro-5-aminomethyl-pyridine, of the formula (II), which is to be used as starting compound is already known (cf. EP-A 391,205).

2-Chloro-5-formylaminomethyl-pyridine, of the formula (III), which is formed in the first reaction step was hitherto unknown from the literature and, being a new compound, is an object of the present patent application.

Formula (IV) provides a general definition of the alkylating agents to be used as starting substances in the second reaction step. In formula (IV), X is preferably chlorine, bromine or iodine, or the group —O—SO$_2$—O—R, and R is preferably straight-chain or branched alkyl having 1 to 6 carbon atoms.

In formula (IV),

X in particular represents bromine or iodine, or the group —O—SO$_2$—O—R, and

R in particular represents methyl, ethyl, propyl, isopropyl, butyl, isobutyl or sec-butyl.

The starting substances of the formula (IV) are known organic chemicals for synthesis.

The 2-chloro-5-(N-alkyl-N-formyl-aminomethyl)-pyridines of the formula (V) which are formed in the second reaction step were hitherto unknown from the literature and, being new compounds, are an object of the present patent application.

In formula (V), R preferably represents straight-chain or branched alkyl having 1 to 6 carbon atoms, in particular methyl, ethyl, propyl, isopropyl, butyl, isobutyl or sec-butyl.

The first steps of the process according to the invention are preferably carried out in the presence of a diluent. Suitable diluents for this purpose are virtually all inert organic solvents. These preferably include aliphatic and aromatic, optionally halogenated hydrocarbons such as hexane, heptane, octane, cyclohexane, methylcyclohexane, benzene, toluene, xylene, chloroform, tetrachloromethane, chlorobenzene and o-dichlorobenzene, as well as ethers such as methyl tert-butyl ether and methyl tert-pentyl ether. Toluene is very particularly preferred as diluent.

The reaction temperatures in the first phase of the process according to the invention—for the formation of 2-chloro-5-formylaminomethyl-pyridine, of the formula (III),—can be varied within a substantial range. The process is generally carried out at temperatures between 20° C. and 200° C., preferably between 50° C. and 150° C.

The process according to the invention is generally carried out under atmospheric pressure. However, it is also possible to carry out the process under increased or reduced pressure at between 0.1 bar and 10 bar.

To carry out the first phase of the process according to the invention, between 1 and 2 moles of formic acid, preferably between 1.1 and 1.5 moles of formic acid, are generally employed per mole of 2-chloro-5-aminomethyl-pyridine, of the formula (II).

The 2-chloro-5-aminomethyl-pyridine, the formic acid and the diluent are generally mixed at room temperature, and the mixture is then heated to the boil until the reaction is complete, preferably while removing the water which has been formed in a water separator. When the reaction solution has cooled to room temperature, it is used directly for carrying out the second step of the process according to the invention.

The second phase of the process according to the invention—formation of 2-chloro-5-(N-alkyl-N-formyl-aminomethyl)-pyridines of the formula (V)—is preferably carried out in the presence of an acid acceptor.

Acid acceptors which can be employed for this purpose are all acid-binding agents which can customarily be used for reactions of this type. The following are preferably suitable: alkali metal hydroxides and alkaline earth metal hydroxides such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates such as sodium carbonate, sodium hydrogen carbonate, potassium carbonate or potassium hydrogen carbonate as well as calcium carbonate, alkali metal acetates such as sodium acetate and potassium acetate, alkali metal alcoholates such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tertbutylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4.3.0]-non-5-ene (DBN), 1,8-diazabicyclo[5.4.0]-undec-7-ene (DBU) and 1,4-diazabicyclo-[2,2,2]-octane (DABCO).

Alkali metal hydroxides, in particular sodium hydroxide and potassium hydroxide, preferably in the form of a 20% strength to 50% strength aqueous solution, are particularly preferred as acid acceptors.

If appropriate, the second phase of the process according to the invention (formation of compounds of the formula (V)) is carried out in the presence of a catalyst. Suitable catalysts for this purpose are, in particular, the so-called phase transfer catalysts such as, for example, triethyl-benzylammonium chloride (TEBA), trimethyl-benzylammonium chloride monium chloride, trimethyl-hexadecylammonium chloride, trioctylmethylammonium chloride, tetrabutylammonium bromide and tetramethylammonoium-hydrogensulphate. The reaction temperatures in the second phase of the process according to the invention can be varied within a substantial range. In general, the process is carried out at temperatures between 0° C. and 100° C., preferably between 10° C. and 80° C.

To carry out the second phase of the process according to the invention, between 1 and 2 moles, preferably between 1.1 and 1.5 moles, of alkylating agent of the formula (IV) are generally employed relative to 1 mole of the initially employed 2-chloro-5-aminomethyl-pyridine, of the formula (II).

The reaction solution resulting from the first process phase is treated with the catalyst and the alkylating agent of the formula (IV), and, if appropriate, more diluent is added; the acid acceptor is then metered in slowly, and the reaction mixture is stirred until the reaction is complete; the mixture is subsequently concentrated. The residue which remains is employed directly to carry out the last reaction step.

The third phase of the process according to the invention—preparation of the 2-chloro-5-alkylaminomethyl-pyridines of the formula (I)—is carried out using an aqueous alkali metal hydroxide solution. 10% strength to 50% strength aqueous solutions of alkali metal hydroxides, in particular of sodium hydroxide or potassium hydroxide, are preferably employed.

The reaction temperatures in the third phase of the process according to the invention can be varied within a substantial range. In general, the process is carried out at temperatures from 20° C. to reflux temperature, preferably between 50° C. and reflux temperature.

To carry out the third phase of the process according to the invention, between 1 and 5 moles, preferably between 1.5 and 2.5 moles, of alkali metal hydroxide are generally employed relative to 1 mole of the initially employed 2-chloro-5-aminomethyl-pyridine, of the formula II.

The residue resulting from the second process phase which contains essentially the intermediate of the formula (V) is treated with the aqueous alkali metal hydroxide solution and the mixture is then stirred at the reaction temperature required until the reaction is complete.

Working-up can be carried out in the customary manner. For example, the mixture is allowed to cool and then extracted with an organic solvent which is virtually immiscible with water such as, for example, toluene, and the solvent is carefully removed from the extraction solution by distillation under reduced pressure, if appropriate after drying. The residue which remains and which essentially contains the product of the formula (I) can be purified further in the customary manner or used directly for further reactions.

The 2-chloro-5-alkylaminomethyl-pyridines of the formula (I) to be prepared by the process according to the invention can be used as intermediates for insecticides (cf. EP-A 302,389 (which corresponds to U.S. Pat. No. 5,175,301, which issued Dec. 29, 1992), EP-A 366,085, EP-A 376,279).

PREPARATION EXAMPLES

Example 1

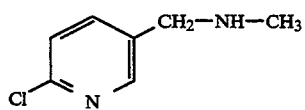

A mixture of 21.5 g (0.15 mol) of 2-chloro-5-aminomethylpyridine, 8.3 g (0.18 mol) of formic acid and 90 ml of toluene is heated at the boil for 1 hour in a water separator. The mixture is subsequently cooled to room temperature (approx. 20° C.), and 0.5 g of triethylbenzylammonium chloride and a solution of 22.7 g (0.18 mol) of dimethyl sulphate in 70 ml of toluene are added. A solution of 30 g (0.75 mol) of sodium hydroxide in 65 ml of water is then metered in slowly, and the reaction mixture is stirred for a further 30 minutes at 20° C.; the toluene is then distilled off. A solution of 12 g (0.3 mol) of sodium hydroxide in 48 ml of water is added to the residue, and the mixture is refluxed for 2 hours. When cold, the mixture is extracted with 2×100 ml of toluene, and the organic extracts are combined, dried using sodium sulphate and filtered. The solvent is carefully removed from the filtrate by distillation first under a waterpump vacuum and then under an oilpump vacuum.

22.5 g of 2-chloro-5-methylaminomethyl-pyridine are obtained as an oily residue. Boiling point: 100°–103° C. at 3 to 4 bar.

Content according to HPLC: 90%; this allows the yield to be calculated as 92% of theory.

The compound 2-chloro-5-ethylaminomethyl-pyridine of boiling point 89°–91° C. at 0.1 to 0.3 bar can be obtained analogously.

I claim:

1. Process for the preparation of 2-chloro-5-alkylaminomethyl-pyridines of the general formula (I)

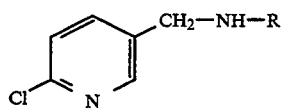

in which
R represents alkyl, wherein 2-chloro-5-aminomethyl-pyridine, of the formula (II),

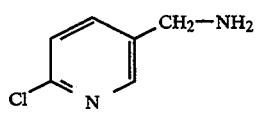

is reacted with formic acid at temperatures between 20° C. and 200° C., if appropriate in the presence of a diluent, the 2-chloro-5-formylaminomethyl-pyridine which has been formed in this process, of the formula (III),

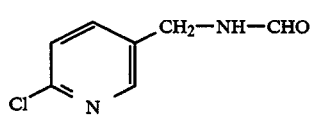

is reacted without intermediate isolation (in situ) with alkylating agents of the general formula (IV)

R—X (IV)

in which
X represents halogen or the group —O—SO$_2$—O—R and
R has the abovementioned meaning, at temperatures between 0° C. and 100° C., if appropriate in the presence of an acid acceptor, if appropriate in the presence of a catalyst and if appropriate in the presence of a diluent, and, finally, the 2-chloro-5-(N-alkyl-N-formyl-aminomethyl)-pyridines thus formed of the general formula (V)

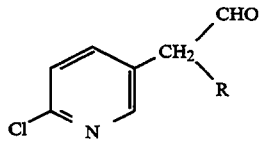

in which
R has the abovementioned meaning, are reacted with aqueous alkali metal hydroxide solution at temperatures between 20° C. and reflux temperature, if appropriate after volatile components have been distilled off.

2. Process according to claim 1 for the preparation of compounds of the formula (I) in which
R represents straight-chain or branched alkyl having 1 to 6 carbon atoms.

3. Process according to claim 1 for the preparation of compounds of the formula (I) in which
R represents methyl, ethyl, propyl, isopropyl, butyl, isobutyl or sec-butyl.

4. Process according to claim 1, wherein 1 and 2 moles of formic acid are employed per mole of 2-chloro-5-aminomethylpyridine, of the formula (II).

5. Process according to claim 1, wherein the formation of compounds of the formula (V) is carried out in the presence of phase transfer catalysts.

6. Process according to claim 1, wherein, in the formation of the compounds of the formula (V), between 1 and 2 moles of alkylating agent of the formula (IV) are employed relative to 1 mole of the initially employed 2-chloro-5-aminomethyl-pyridine (II).

7. Process according to claim 1, wherein, in the third phase of the process, between 1 and 5 moles of alkali metal hydroxide are employed relative to 1 mole of the initially employed 2-chloro-5-aminomethyl-pyridine (II).

8. Process according to claim 7, wherein a 10 to 50% strength aqueous solution of alkali metal hydroxides is employed.

9. 2-Chloro-5-formylaminomethyl-pyridine, of the formula (III)

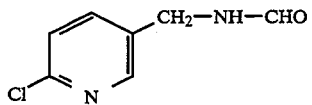

10. 2-Chloro-5-(N-alkyl-N-formyl-aminomethyl)-pyridines of the formula (IV)

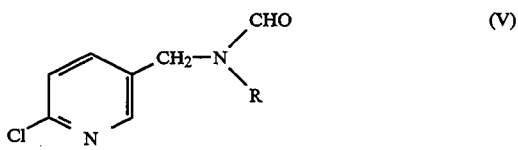

in which
R represents alkyl.

* * * * *